United States Patent
Mosa et al.

(10) Patent No.: US 11,805,773 B1
(45) Date of Patent: Nov. 7, 2023

(54) NANOCOMPOSITE INCLUDING WATER-SOLUBLE NANO-POLYMER AND MESOPOROUS SILICA NANOPARTICLES ENCAPSULATED WITH AZOLE DERIVATIVES

(71) Applicant: KING FAISAL UNIVERSITY, Al-Ahsa (SA)

(72) Inventors: Mohamed Ahmed Mosa, Al-Ahsa (SA); Sherif Mohamed El-Ganainy, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/211,252

(22) Filed: Jun. 17, 2023

(51) Int. Cl.
| | |
|---|---|
| *A01N 43/78* | (2006.01) |
| *A61K 47/36* | (2006.01) |
| *A61P 35/00* | (2006.01) |
| *C01B 33/18* | (2006.01) |
| *C07D 417/04* | (2006.01) |
| *A01P 3/00* | (2006.01) |
| *A01N 25/10* | (2006.01) |
| *A01N 25/12* | (2006.01) |
| *A61K 9/51* | (2006.01) |

(52) U.S. Cl.
CPC ............ *A01N 43/78* (2013.01); *A01N 25/10* (2013.01); *A01N 25/12* (2013.01); *A01P 3/00* (2021.08); *A61K 9/5161* (2013.01); *C01B 33/18* (2013.01); *C07D 417/04* (2013.01)

(58) Field of Classification Search
CPC ....... A01N 43/78; C01B 33/18; A61K 9/5161
See application file for complete search history.

(56) References Cited

FOREIGN PATENT DOCUMENTS

| | | |
|---|---|---|
| CN | 113229257 A | 8/2021 |
| WO | 2017085636 A1 | 5/2017 |

OTHER PUBLICATIONS

Abdelsalam et al. J Enzyme Inhibition and Medicinal Chemistry, 2022, 37(1), 2265-2282.*
Venzke et al., Ultrasonics Sonochemistry, 18, 2011, 370-374.*
Cao et al., "Quaternized Chitosan-Capped Mesoporous Silica Nanoparticles as Nanocarriers for Controlled Pesticide Release," Nanomaterials 6(7): 126 (2016).
Buchman et al., "Chitosan-Coated Mesoporous Silica Nanoparticle Treatment of *Citrullus lanatus* (Watermelon): Enhanced Fungal Disease Suppression and Modulated Expression of Stress-Related Genes," ACS Sustainable Chem. Eng.2019, 7, 24, 19649-19659.

* cited by examiner

*Primary Examiner* — Kyle A Purdy
(74) *Attorney, Agent, or Firm* — Nath, Goldberg & Meyer; Richard C. Litman

(57) ABSTRACT

A nanocomposite including a water-soluble nano-polymer and mesoporous silica nanoparticles encapsulated with an azole derivative can be used an antifungal agent against a wide range of phytopathogenic fungi. The azole derivative has the following structural formula

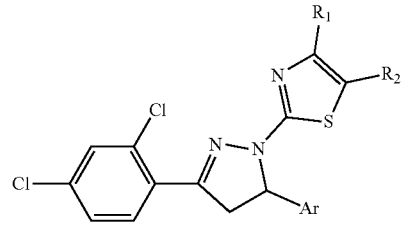

wherein R is selected from the group consisting of OMe and H;

wherein $R_1$ is OMe; and wherein $R_2$ is selected from the group consisting of H and Cl.

20 Claims, No Drawings

NANOCOMPOSITE INCLUDING WATER-SOLUBLE NANO-POLYMER AND MESOPOROUS SILICA NANOPARTICLES ENCAPSULATED WITH AZOLE DERIVATIVES

BACKGROUND

1. Field

The disclosure of the present patent application relates to fungicidal agents, and particularly, to a nanocomposite fungicidal agent including a water-soluble nano-polymer and mesoporous silica nanoparticles encapsulated with azole derivatives.

2. Description of the Related Art

Huge amounts of chemical fungicides are applied globally to protect crops from fungal diseases. Traditional fungicide formulations are based on adhesives and adjuvants, which do not have selective or interactive release ability in the presence of the targeted pests.

Synthetic fungicides are considered the most effective solution against a wide range of fungal diseases. However, their long-term use has induced undesirable pathogen resistance. Besides, their residues in soil and food are detrimental to human beings and the environment. Thus, there is a need for an alternative, eco-safe antifungal agent with smart and efficient behavior in plant disease control. The search for eco-friendly smart pesticide alternatives has become a global demand trend to maximize pesticide employment and minimize the potential risk to the environment and humans. Many pesticides do not offer control on where and when pesticide release will happen.

Additionally, since the discovery of corn late wilt disease (LWD), caused by *Magnaporthiopsis maydis*, in Egypt in the early 1960s, worldwide scientific efforts have led to much progress in understanding the disease mode, with a continued search to find a completely efficient control agent for this destructive disease. Late wilt, or black bundle disease, is a vascular wilt disease of *Zea mays* L. (corn, maize) caused by the soil-borne and seed-borne fungus *Magnaporthiopsis maydis*, with the synonyms *Harpophora maydis*, *Acremonium maydis*, and *Cephalosporium maydis* (Samra, Sabet, and Hingorani). To date, late wilt has been reported in about 10 countries. Without any effective fungicide to completely control it, this disease has resulted in significant economic losses in Egypt, India, Spain, Portugal, and Israel. Late wilt is considered to be the most destructive disease in maize-growing areas in those countries, with up to 100% infection and total yield loss reported in some fields. In Egypt for example, the cultivated maize area covered about 880,000 ha and yielded almost 7.2 million metric tons of grains, with a degree of loss that may reach up to 80-100% in infested fields.

It is common to provide seeds with a coating to protect the seeds from damage during handling, fungal disease infection, and to prevent dust and give a cosmetic appearance. Such coatings can also afford the advantages of protecting the seeds from pests and disease, as well as smoothing the seed surface to make planting easier. In order to control seed germination, or the germination rate, plant nutrients or other growth stimulating agents can be incorporated into the seed coating. Plant protecting agents, such as pesticides (e.g., fungicides and insecticides), may be incorporated to further protect the seed from disease and/or pest attack. Conventional liquid seed coatings are generally sticky, however, and cause seeds to stick to each other and to contact surfaces, preventing easy flow of the coated seeds.

The discovery of highly aggressive *M. maydis* isolates is a constant problem. These fungal strains may threaten resistant maize cultivars. Indeed, growing resistance cultivars for extended periods in the same location may lead to gradual LWD susceptibility weakening.

Resistance to chemical fungicides has been detected in many fungal pathogens exposed to fungicides applied for disease control in various plants, such as tomato, corn, pepper, and strawberry plants, for example. In addition, the market and regulatory pressures on chemical residues in the environment and in human health have grown significantly, which leads to the need to develop new control techniques in the production system.

Thus, a nanocomposite including water soluble nano-polymer and mesoporous silica nanoparticles (MSN) encapsulated with a substituted azole derivative solving the aforementioned problems is desired.

SUMMARY

The present subject matter relates to a nanocomposite comprising a water-soluble nano-polymer and mesoporous silica nanoparticles encapsulated within an azole derivative, the azole derivative having the formula I:

Formula I wherein, $R_1$ is selected from methyl and substituted phenyl; $R_2$ is selected from the group consisting of hydrogen, acetyl, ethyl carboxylate, N-phenyl carboxamide, phenyldiazenyl, p-tolyldiazenyl, and 4-(chlorophenyl) diazenyl; and Ar is 4-methoxyphenyl or 3,4-dimethoxyphenyl.

In an embodiment, the nanocomposite can be useful as an antifungal agent against a wide range of phytopathogenic fungi selected from the group consisting of *Fusarium oxysporum* f. sp. *lycopersici* (the causal agent of *Fusarium* wilt disease in tomatoes), *Fusarium solani* (the causal agent of foot rot disease of tomatoes), *Sclerotinia sclerotiorum* (the causal agent of *Sclerotinia* stem rot disease), *Botrytis cinerea* (the causal agent of tomato gray mold disease), *Macrophomina phaseolina* (the causal agent of stem and root rot, charcoal rot and seedling blight), and *Magnaporthiopsis maydis* (the causal agent of late wilt disease in maize).

In another embodiment, the present subject matter relates to a fungicidal composition, comprising the nanocomposite as described herein and a carrier.

In a further embodiment, the present subject matter relates to a method of inhibiting fungal growth in a plant, comprising: administering an effective amount of a fungicidal composition including a nanocomposite and a carrier to a plant in need thereof, the nanocomposite comprising chitosan nanoparticles and mesoporous silica nanoparticles encapsulated within an azole derivative, the azole derivative having the formula I:

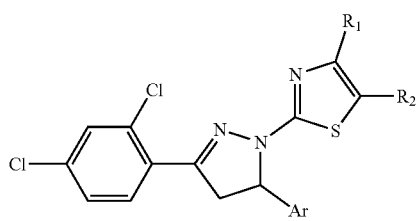

Formula I wherein, $R_1$ is selected from methyl and substituted phenyl; $R_2$ is selected from the group consisting of hydrogen, acetyl, ethyl carboxylate, N-phenyl carboxamide, phenyldiazenyl, p-tolyldiazenyl, and 4-(chlorophenyl) diazenyl; and Ar is 4-methoxyphenyl or 3,4-dimethoxyphenyl.

According to an embodiment, a method of inhibiting fungal growth in a plant can include administering an effective amount of a fungicidal composition including a nanocomposite and carrier to a plant in need thereof, the nanocomposite including chitosan nanoparticles and mesoporous silica nanoparticles encapsulated within an azole derivative, the azole derivative having the formula I:

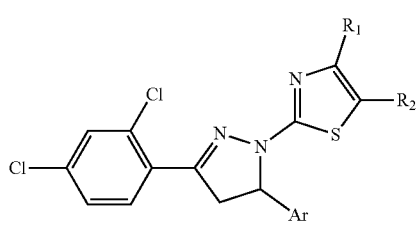

Formula I wherein, $R_1$ is selected from methyl and substituted phenyl; $R_2$ is selected from hydrogen, acetyl, ethyl carboxylate, N-phenyl carboxamide, phenyldiazenyl, p-tolyldiazenyl, and 4-(chlorophenyl) diazenyl; and Ar is 4-methoxyphenyl or 3,4-dimethoxyphenyl.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

In an embodiment, the present subject matter relates to a nanocomposite comprising a water-soluble nano-polymer and mesoporous silica nanoparticles encapsulated within an azole derivative, the azole derivative having the formula I:

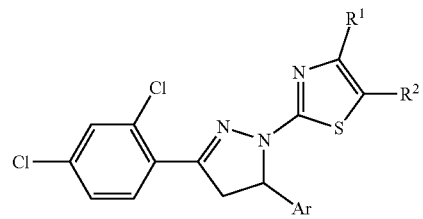

Formula I wherein,
$R_1$ is selected from methyl and substituted phenyl;
$R_2$ is selected from the group consisting of hydrogen, acetyl, ethyl carboxylate, N-phenyl carboxamide, phenyldiazenyl, p-tolyldiazenyl, and 4-(chlorophenyl) diazenyl; and Ar is 4-methoxyphenyl or 3,4-dimethoxyphenyl.

The nanocomposite can be used as an anti-fungal agent for treating or inhibiting a fungal infection in a plant. The fungal infection can be caused by at least one of seed-borne, air-borne, and/or soil-borne fungi. According to an embodiment, the fungal infection can be caused by a fungal pathogen selected from the group consisting of *Fusarium oxysporum, Fusarium solani, Alternaria solani, Alternaria alternata, Macrophomina phaseolina, Rhizoctonia solani, Verticillium dahliae, Magnaporthiopsis maydis, Fusarium verticillioides, Botrytis cinerea*, and any combination thereof.

The nanocomposite can exhibit "smart" release behavior such that release of the pesticide can be controlled to occur in the presence of a pathogenic agent. The nanocomposite offers an environmentally responsible, all-natural, and biodegradable substitute to reduce and/or completely replace the use of synthetic fungicides. The nanocomposite can prevent or control either soil, vascular, or seed fungal infestations, thereby protecting crops, both growing and harvested, from the damages caused by infestation and infection due to phytopathogenic fungi. According to an embodiment, the nanocomposite can have a particle size ranging from about 40 nm to about 50 nm.

According to an embodiment, the nano-polymer, i.e., the water-soluble nano-polymer, can be disposed or deposited within pores of the mesoporous silica nanoparticles. According to an embodiment, the nano-polymer can be a water-soluble polymer or biopolymer. In an embodiment, the water-soluble nano-polymer can be chitosan. According to an embodiment, the biopolymer can be a quaternized chitosan. In an embodiment, the quaternized chitosan is N-(2-Hydroxyl) propyl-3-tri-methyl-ammonium CS chloride "HTCC."

According to an embodiment, the mesoporous silica nanoparticles can be functionalized with β-glucan and/or —$NH_2$ surface modified mesoporous silica nanoparticles. According to an embodiment, the mesoporous silica nanoparticles can have a particle size ranging from about 10 nm to about 30 nm. For example, a particle size of the mesoporous silica nanoparticles can be about 10 nm, about 15 nm, about 20 nm, about 25 nm, or about 30 nm.

According to an embodiment, the surface of the mesoporous silica nanoparticles can be functionalized or modified with a layer double hydroxide nanosheet (LDH) (a biodegradable adsorbent nanohybrid agent).

In an embodiment, the azole derivative in the nanocomposite can have the formula Ia:

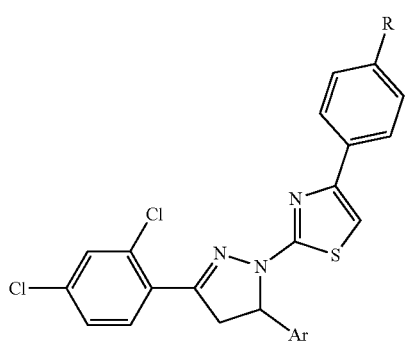

Formula Ia wherein,
R is H or Cl; and
Ar is 4-methoxyphenyl or 3,4-dimethoxyphenyl.

According to an embodiment, the azole derivative in the nanocomposite can be selected from the group consisting of:

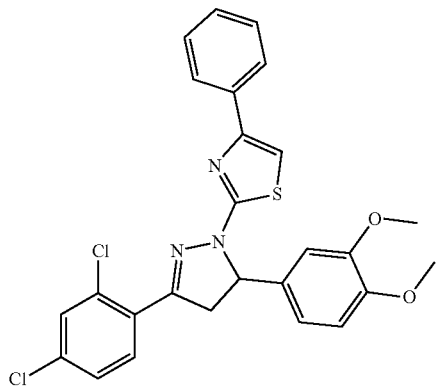

2-(3-(2,4-dichlorophenyl)-5-(3,4-dimethoxyphenyl)-4,5-dihydro-1H-pyrazol-1-yl)-4-phenylthiazole (1a);

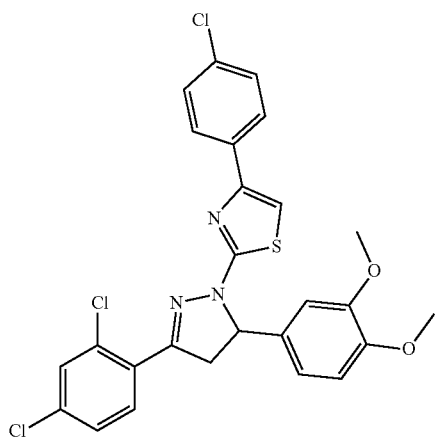

4-(4-chlorophenyl)-2-(3-(2,4-dichlorophenyl)-5-(3,4-dimethoxyphenyl)-4,5-dihydro-1H-pyrazol-1-yl)thiazole (1b);

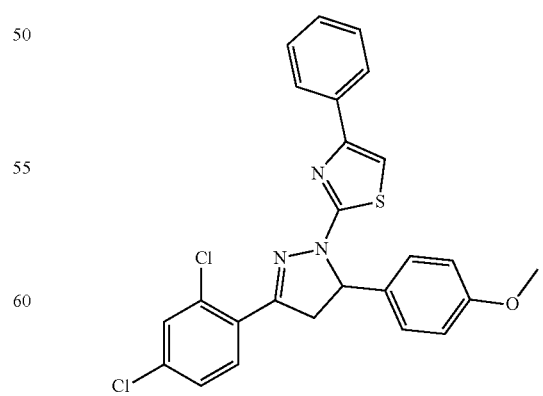

2-(3-(2,4-dichlorophenyl)-5-(4-methoxyphenyl)-4,5-dihydro-1H-pyrazol-1-yl)-4-phenylthiazole (1c); and

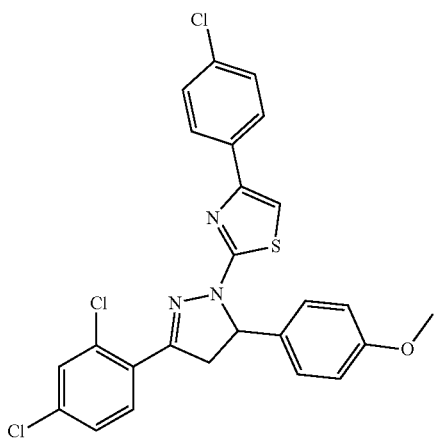

4-(4-chlorophenyl)-2-(3-(2,4-dichlorophenyl)-5-(4-methoxyphenyl)-4,5-dihydro-1H-pyrazol-1-yl)thiazole (1d).

According to an embodiment, a ratio of the azole derivative to the mesoporous silica nanoparticles in the nanocomposite can be 2:1.

An embodiment of the present subject matter is directed to a fungicidal composition comprising the nanocomposite and an acceptable carrier. According to an embodiment, the carrier can include at least one of a coloring agent and an anti-foaming agent. According to an embodiment, the fungicidal composition can optionally be used in combination with other additional pesticides to increase the pest control spectrum. Other pesticides useful in this regard can include, but are not limited to, various insecticides, fungicides, nematicides, acaricides, molluscicides, and bactericides.

According to an embodiment, the fungicidal composition can include one or more coloring agents, e.g., dye or pigmented colorants. In an embodiment, the fungicidal composition can include a dye selected from the group consisting of anthraquinone, triphenyl methane, phthalocyanine, phthalocyanine derivatives, diazonium salts, and any combination thereof. In an embodiment, the fungicidal composition can include a pigment selected from the group consisting of pigment red 112 (CAS number 6535-46-2), pigment red 2 (CAS number 6041-94-7), pigment red 48:2 (CAS number 7023-61-2), pigment blue 15:3 (CAS number 147-14-8), pigment green 36 (CAS number 14302-13-7), pigment green 7 (CAS number 1328-53-6), pigment yellow 74 (CAS number 6358-31-2), pigment orange 5 (CAS number 3468-63-1), pigment violet 23 (CAS number 6358-301), and any combination thereof. According to an embodiment, the fungicidal composition can include from about 0% to about 50% by weight of the coloring agent.

According to an embodiment, the pigment is an effect pigment, such as a pearlescent pigment or aluminum. The effect pigments typically have particle sizes of no more than about 200 μm, for example, no more than about 100 μm. In an embodiment, the fungicidal composition can include a pearlescent pigment having a particle size of about 15 μm or less or about 60 μm or less and at least about 1 μm in size.

According to an embodiment, the fungicidal composition can include an anti-foaming agent selected from the group consisting of polyethylene glycol, glycerine, mineral oil defoamers, silicone defoamers, non-silicone defoamers (such as polyethers, polyacrylates), dimethylpolysiloxanes (silicone oils), arylalkyl modified polysiloxanes, polyether siloxane copolymer containing fumed silica, and any combination thereof. According to an embodiment, the fungicidal composition can include from about 0.1% to about 0.3% by weight of the anti-foaming agent.

According to an embodiment, the present subject matter relates to a method of inhibiting fungal growth in a plant that can include administering an effective amount of a fungicidal composition including a nanocomposite to a plant in need thereof, the nanocomposite including chitosan nanoparticles and mesoporous silica nanoparticles encapsulated within an azole derivative, the azole derivative having the formula I:

Formula I

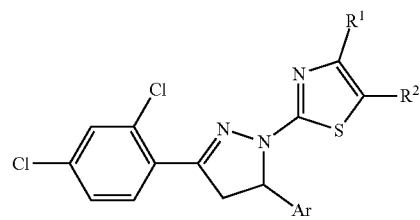

wherein,
$R_1$ is selected from methyl and substituted phenyl;
$R_2$ is selected from the group consisting of hydrogen, acetyl, ethyl carboxylate, N-phenyl carboxamide, phenyldiazenyl, p-tolyldiazenyl, and 4-(chlorophenyl) diazenyl; and
Ar is 4-methoxyphenyl or 3, 4-dimethoxyphenyl.

In an embodiment, the azole derivative used in the present methods has the formula Ia:

Formula Ia

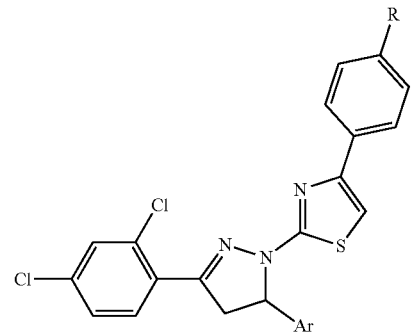

wherein,
R is H or Cl; and
Ar is 4-methoxyphenyl or 3,4-dimethoxyphenyl.

In an embodiment, the azole-derivative useful in the present methods is selected from the group consisting of 2-(3-(2,4-dichlorophenyl)-5-(3,4-dimethoxyphenyl)-4,5-dihydro-1H-pyrazol-1-yl)-4-phenylthiazole (1a); 4-(4-chlorophenyl)-2-(3-(2,4-dichlorophenyl)-5-(3,4-dimethoxyphenyl)-4,5-dihydro-1H-pyrazol-1-yl)thiazole (1b); 2-(3-(2,4-dichlorophenyl)-5-(4-methoxyphenyl)-4,5-dihydro-1H-pyrazol-1-yl)-4-phenylthiazole (1c); and 4-(4-chlorophenyl)-2-(3-(2,4-dichlorophenyl)-5-(4-methoxyphenyl)-4,5-dihydro-1H-pyrazol-1-yl)thiazole (1d).

In an embodiment, administering the fungicidal composition can include contacting the plant, a seed of the plant, or a soil surrounding the plant seed with the fungicidal composition. According to an embodiment, the fungal infection is caused by a fungal pathogen selected from the group consisting of *Fusarium oxysporum, Fusarium solani, Alternaria solani, Alternaria alternata, Macrophomina phaseolina, Rhizoctonia solani, Verticillium dahliae, Magnaporthiopsis maydis, Fusarium verticillioides, Botrytis cinerea*, and combinations thereof.

In an embodiment, the fungicidal composition can achieve anti-fungal efficiency against different fungal plant pathogens, including, for example, *F. oxysporum* f. sp. *lycopersici* (FOL), the causal agent of *Fusarium* wilt in tomato plants, and *Magnaporthiopsis maydis*, the causal agent of late wilt disease of maize plants.

According to an embodiment, the nanocomposite can be used as a seed coating protectant agent against seed borne fungi infecting corn, wheat, soybean, canola, sunflower, edible beans, peas, alfalfa, and tomato seeds. According to an embodiment, the seed coating protectant agent can protect against corn late wilt disease. In an embodiment, corn seeds coated with the nanocomposite can be completely protected from late wilt disease starting from their seedling stage until harvesting stage.

According to an embodiment, in planta, under natural infection conditions, administering an amount of about 1 mg/L to about 5 mg/L of the nanocomposite to a plant infected with a fungal disease can significantly reduce severity of the infection without any phytotoxicity. In an embodiment, administering about 1 mg/L of the nanocomposite to maize seeds for about 120 days can reduce maize late wilt severity below about 1%, without any phytotoxicity. In an embodiment, administering about 5 mg/L to tomato plants for about 75 days can reduce *Fusarium* wilt disease severity below about 1%, without any phytotoxicity.

The nanocomposite can be a biodegradable, "smart" delivery system which can stimulate favorable biological responses in plants when administered in the recommended dosages. The nanocomposite can provide a cost-effective and environmentally benign nano-pesticide for long-term plant protection.

In another embodiment, the present subject matter relates to an azole derivative having the formula I:

Formula I wherein, $R_1$ is selected from methyl and substituted phenyl;

$R_2$ is selected from the group consisting of hydrogen, acetyl, ethyl carboxylate, N-phenyl carboxamide, phenyldiazenyl, p-tolyldiazenyl, and 4-(chlorophenyl) diazenyl; and Ar is 4-methoxyphenyl or 3, 4-dimethoxyphenyl.

In this regard, in certain embodiments, the phenyl of $R_1$ can be substituted with, for example, an alkyl group, an alkoxy group, a halide, and the like. In other embodiments, the phenyl of $R_1$ can be substituted with a halide, for example, a chlorine, bromine, fluorine, or the like. In an embodiment, the halide can be chlorine.

In an embodiment, the azole derivative can have the formula Ia:

Formula Ia 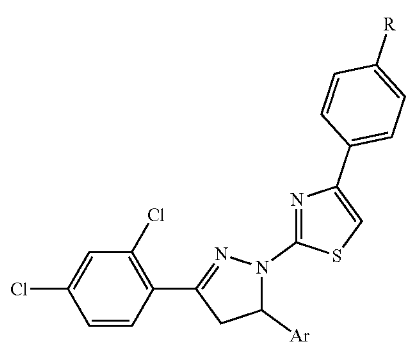 wherein,

R is H or Cl; and

Ar is 4-methoxyphenyl or 3,4-dimethoxyphenyl.

In an embodiment, the azole-derivative is selected from the group consisting of 2-(3-(2,4-dichlorophenyl)-5-(3,4-dimethoxyphenyl)-4,5-dihydro-1H-pyrazol-1-yl)-4-phenylthiazole (1a); 4-(4-chlorophenyl)-2-(3-(2,4-dichlorophenyl)-5-(3,4-dimethoxyphenyl)-4,5-dihydro-1H-pyrazol-1-yl)thiazole (1b); 2-(3-(2,4-dichlorophenyl)-5-(4-methoxyphenyl)-4,5-dihydro-1H-pyrazol-1-yl)-4-phenylthiazole (1c); and 4-(4-chlorophenyl)-2-(3-(2,4-dichlorophenyl)-5-(4-methoxyphenyl)-4,5-dihydro-1H-pyrazol-1-yl)thiazole (1d).

An embodiment of the present subject matter is directed to a method of making a fungicidal composition including mixing the nanocomposite with an acceptable carrier. For example, the method of making a fungicidal composition can include mixing the nanocomposite under sterile conditions with an acceptable carrier, preservatives, buffers, and/or propellants to create the fungicidal composition.

To prepare the fungicidal composition, the nanocomposite, as the active ingredient, is intimately admixed with an acceptable carrier. Carriers are inert excipients, including, but not limited to, binders, suspending agents, lubricants, flavorings, sweeteners, preservatives, coloring agents, antifoaming agents, and coatings.

The present compositions can be provided in any suitable form, e.g., powders or liquid sprays. The composition can be presented in a form suitable for daily, weekly, or monthly administration. An effective amount of the composition or an amount effective to treat a plant disease, such as a fungal infection, may be determined initially from the Examples described herein and adjusted for specific targeted diseases using routine methods.

The present teachings are illustrated by the following examples.

EXAMPLES

Example 1

Syntheses Process for Azole Derivative 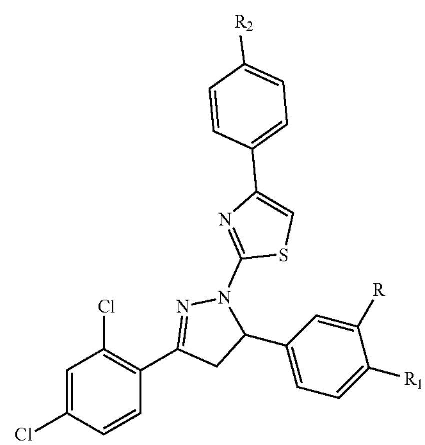 1a-d

| 1 | R | $R_1$ | $R_2$ |
|---|---|---|---|
| a | OMe | OMe | H |
| b | OMe | OMe | Cl |
| c | H | OMe | H |
| d | H | OMe | Cl |

For synthesis of the azole derivatives above, a solution of 2,4-dichloroacetophenone (1) (1.76 g, 9.3 mmol) and an appropriate aldehyde (9.3 mmol) in absolute ethanol (40 mL), 10% sodium hydroxide solution (15 mL) was added portion wise. The mixture was stirred for 6 h at room temperature. The separated precipitate was filtered, washed with water, dried and crystallized from ethanol to afford compounds, namely (1-(2,4-dichlorophenyl)-3-(3,4-dimethoxyphenyl)prop-2-en-1-one and 1-(2,4-dichlorophenyl)-3-(4-methoxyphenyl)prop-2-en-1-one, in 87% yield as a yellow powder. Then, a mixture from the above mentioned two compounds (1 mmol) and thiosemicarbazide (1 mmol) in absolute ethanol (50 mL), and sodium hydroxide (0.29 g, 7 mmol) were added. The reaction mixture was heated under reflux with stirring for 6 h. After cooling, the formed product was filtered, washed with ethanol, dried, and crystallized from ethanol to give the corresponding pyrazoline compound, namely (3-(2,4-dichlorophenyl)-5-(3,4-dimethoxyphenyl)-4,5-dihydro-1H-pyrazole-1-carbothioamide.

A mixture of carbothioamides (1 mmol) and the appropriate 1-aryl-2-bromoethanone (1.1 mmol) in absolute ethanol (20 mL) was heated under reflux for 4 h. After cooling, the formed precipitate was filtered and crystallized from ethanol to afford the corresponding compounds 1a-d.

2-(3-(2,4-dichlorophenyl)-5-(3,4-dimethoxyphenyl)-4,5-dihydro-1H-pyrazol-1-yl)-4-phenylthiazole (1a): Yellowish powder in 74% yield, m.p. 120-122° C.; IR (KBr, ν cm$^{-1}$): 1584 (C=N); $^1$H NMR (DMSO-d$_6$, 400 MHz) δ ppm: 3.50 (dd, J=8, 17.6 Hz, 1H, H$_A$), 3.72 (s, 3H, OC$\underline{H}_3$), 3.78 (s, 3H, OC$\underline{H}_3$), 4.12 (dd, J=12.4, 17.6 Hz, 1H, H$_M$), 5.64 (dd, J=7.2, 12.4 Hz, 1H, H$_X$), 6.92-7.09 (m, 3H, Ar—H), 7.26-7.38 (t, 4H, 3 Ar—H, thiazole H), 7.56 (dd, J=2.8, 9.2 Hz, 1H, Ar—H), 7.76-7.78 (m, 3H, Ar—H), 7.82 (d, J=8.8 Hz, 1H, Ar—H); $^{13}$C NMR (DMSO-d$_6$, 100 MHz) δ ppm: 45.8 (C$\underline{H}_2$ pyrazoline), 55.9 (2OC$\underline{H}_3$), 64.7 (C$\underline{H}$ pyrazoline), 105.2, 111.6, 112.3, 119.2, 126.0 (2C), 128.1, 128.2, 129.0, 129.4 (2C), 130.8, 132.3, 132.9, 134.2, 134.9, 135.0, 148.8, 149.0, 150.8, 151.0, 164.77; MS (EI) m/z (%): 510.00 (M$^+$, 15.80), 96.39 (100); Anal. Calcd. for C$_{26}$H$_{21}$Cl$_2$N$_3$O$_2$S (510.43): C, 61.18; H, 4.15; N, 8.23; Found; C, 61.02; H, 4.39; N, 8.47.

4-(4-chlorophenyl)-2-(3-(2,4-dichlorophenyl)-5-(3,4-dimethoxyphenyl)-4,5-dihydro-1H-pyrazol-1-yl)thiazole (1b): Yellowish white powder in 79% yield, m.p. 158-159° C.; IR (KBr, ν cm$^{-1}$): 1584 (C=N); $^1$H NMR (DMSO-d$_6$, 400 MHz) δ ppm: 3.48 (dd, J=8, 15.2 Hz, 1H, H$_A$), 3.72 (s, 3H, OC$\underline{H}_3$), 3.76 (s, 3H, OC$\underline{H}_3$), 4.11 (dd, J=9.6, 14.8 Hz, 1H, H$_M$), 5.62 (dd, J=9.2, 15.2 Hz, 1H, H$_X$), 6.93 (s, 2H, Ar—H), 7.06 (s, 1H, Ar—H), 7.40-7.43 (m, 3H, 2Ar—H and thiazole H), 7.54 (d, J=7.6 Hz, 1H, Ar—H), 7.75-7.81 (m, 4H, Ar—H); MS (EI) m/z (%): 544.49 (M$^+$, 21.11), 218.49 (100); Anal. Calcd. for C$_{26}$H$_{20}$Cl$_3$N$_3$O$_2$S (544.88): C, 57.31; H, 3.70; N, 7.71; Found; C, 57.53; H, 3.86; N, 7.89.

2-(3-(2,4-dichlorophenyl)-5-(4-methoxyphenyl)-4,5-dihydro-1H-pyrazol-1-yl)-4-phenylthiazole (1c): Yellow powder in 69% yield, m.p. 72-75° C.; IR (KBr, ν cm$^{-1}$): 1583 (C=N); $^1$H NMR (DMSO-d$_6$, 400 MHz) δ ppm: 3.38-3.44 (m, 1H, H$_A$), 3.70 (s, 3H, OC$\underline{H}_3$), 4.05-4.12 (m, 1H, H$_M$), 5.64 (s, 1H, H$_X$), 6.91 (d, J=8.8, 2H, Ar—H), 7.26-7.35 (m, 6H, 5 Ar—H and thiazole H), 7.51 (d, J=12 Hz, 1H, Ar—H), 7.69-7.79 (m, 4H, Ar—H); MS (EI) m/z (%): 480.13 (M$^+$, 16.80), 76.10 (100); Anal. Calcd. for C$_{25}$H$_{19}$Cl$_2$N$_3$OS (480.41): C, 62.50; H, 3.99; N, 8.75; Found; C, 62.41; H, 4.17; N, 8.82.

4-(4-chlorophenyl)-2-(3-(2,4-dichlorophenyl)-5-(4-methoxyphenyl)-4,5-dihydro-1H-pyrazol-1-yl)thiazole (1d): Yellowish powder in 75% yield, m.p. 140-141° C.; IR (KBr, ν cm$^{-1}$): 1583 (C=N); $^1$H NMR (DMSO-d$_6$, 400 MHz) δ ppm: 3.42-3.46 (m, 1H, H$_A$), 3.72 (s, 3H, OC$\underline{H}_3$), 4.10 (dd, J=12, 17.6 Hz, 1H, H$_M$), 5.63 (dd, J=5.2, 14 Hz, 1H, H$_X$), 6.91 (d, J=8.8 Hz, 2H, Ar—H), 7.34-7.42 (m, 5H, Ar—H and thiazole H), 7.53 (d, J=10.4 Hz, 1H, Ar—H), 7.72-7.80 (m, 4H, Ar—H); $^{13}$C NMR (DMSO-d$_6$, 100 MHz) δ ppm: 45.8 (C$\underline{H}_2$ pyrazoline), 55.5 (OC$\underline{H}_3$), 64.3 (CH pyrazoline), 106.0, 114.4 (2C), 127.7 (2C), 128.1, 128.5 (2C), 129.0 (2C), 129.2, 130.9, 132.2, 132.5, 132.9, 133.7, 133.7, 135.0, 149.8, 150.8, 159.2, 164.8; MS (EI) m/z (%): 514.26 (M$^+$, 10.28), 89.34 (100); Anal. Calcd. for C$_{25}$H$_{18}$Cl$_3$N$_3$OS (514.85): C, 58.32; H, 3.52; N, 8.16; Found; C, 58.44; H, 3.76; N, 8.41.

Example 2

Synthesis of β-Glucan-NH$_2$ Surface Modified Mesoporous Silica Nanoparticles

For the preparation of the mesoporous silica nanoparticles (MSNs), MSNs were synthesized with 10 nm size under alkaline conditions using Cetyl-tri-methyl-ammonium bromide (CTAB) which acted as the structure-directing agent, and TEOS solution as the precursor of silica. 2.75 g of CTAB was first dissolved slowly in a mixture solution of 520 mL of deionized water (dH$_2$O), and 3.5 mL of 2.0 M sodium hydroxide (NaOH) under 500 rpm magnetic stirring at room temperature. The temperature of the solution was then raised to 80° C. in an oil bath, then about 5 mL of tetra-ethoxysilane (TEOS) solution was added at a rate of 10 drops/min followed by dropwise addition of 0.85 mL TSD. At 80° C., the mixed solution was vigorously agitated for almost 3 hours. The white precipitate (purified MSNs) that formed throughout the operation was rinsed three times with ethyl alcohol followed by water.

After preparation of the MSNs, 20 mg of the MSNs were disseminated in the synthetic compound derivatives (1a-d) in methanol solution (0.1 mg/mL, 1.0 mL). Then, the suspension was sonicated for 30 min at low power, followed by vacuum-freeze-drying. The produced powdered mesoporous silica nanoparticles were then calcined at 550° C. for 7 h to entirely eliminate the surfactant.

In order to modify the MSN surface, in 50 mL of toluene, 0.5 g of the obtained template-free MSNs was suspended and kept under reflux at 110° C. with magnetic stirring. After 30 min, 1 mL of APTES was added. The same conditions were maintained for 24 h. The surface-modified MSNs-NH$_2$ were centrifuged, washed with 80% EtOH aqueous solution, and finally dehydrated in the oven at 60° C.

For smart delivery, the MSNs-NH$_2$ were functionalized using β-glucan carboxymethylation. 10 g of β-glucan was mixed with 120 mL of isopropyl alcohol and 12.6 mL of NaOH solution (7.5 mol L$^{-1}$). At 10° C., the mix was continuously stirred for 1 h. 3.95 g of sodium chloro-acetate dispersed in 14 mL of deionized water was dropped into the mixture to generate sodium chloro-acetate β-glucan. The temperature was raised to 70° C. and stirred for 2 h. Then, 6 mol L$^{-1}$ hydrochloric acid solution was added to neutralize the excessive NaOH, and the resulting salts were eliminated by dialyzing the obtained residue for 72 h in deionized water. The non-dialyzed residual portion was lyophilized. Finally, in 15 mL acetone containing 5 g of dry sodium chloroacetate β-glucan, 30 mL of 6 mol HCl solution was added to convert sodium chloroacetate β-glucan to β-glucan-COOH. The mix was held while stirring for 30 minutes.

The resulting β-glucan-COOH was cleaned multiple times with a washing solution of methanol:water (4:1) and dried in a vacuum at 50° C.

Example 3

β-Glucan-MSNs-NH$_2$ Nanocomposite Synthesis

A layer double hydroxide (LDH) was synthesized with 0.075 mol of magnesium lactate trihydrate and 0.025 mol of aluminum lactate, which were dissolved in ion-exchanged water heated to 60 C and kept at a constant volume of 500 mL. An Mg—Al-mixed solution with a Mg/Al mole ratio of 3.0 was prepared. A total of 0.25 mol of lactate was kept at a constant volume of 500 mL in ion-exchanged water, and a lactate solution of 0.5 mol/L was prepared. A total of 500 mL of aqueous lactate solution was placed in a five-neck flask, and 600 mL of the Mg—Al-mixed solution was dripped at 10 mL/min while stirring at 60° C. under nitrogen circulation. During this time, a pH of 10.5 was maintained by dripping 1.25 mol/L of NaOH solution. The solution was stirred for 1 hour when the Mg—Al-mixed solution was dripped, followed by the centrifugation of suspension and the decompression drying of the obtained solid phases for 24 hours, resulting in the final product.

In order to obtain LDH nanosheets, a total of 100 mL of N$_2$-purged ion-exchanged water was placed in a three-neck flask, including 10.0 g of either pre-dried lactate Mg—Al LDH or NO$_3$·Mg—Al LDH. The three-neck flask was placed in an oil bath and underwent heat reflux for 24 h at 120° C., followed by ultrasonic treatment for 5 h at 43 kHz and 40° C. The obtained suspensions were centrifuged at 3000 rpm for 10 min, and the supernatant solution was acquired.

Secondly, about 2.5 mL of quaternized chitosan, N-(2-Hydroxyl) propyl-3-tri-methyl-ammonium CS chloride "HTCC" aqueous solution (20 mg/mL) was added to the suspension of the functionalized β-glucan-MSNs-NH$_2$ nanocomposite encapsulated with the synthetic compound derivatives in dropwise manner while it was sonified. Within 10 min of more sonification, the β-glucan-MSNs-NH$_2$ nanocomposite encapsulated with the synthetic compound derivatives doped-HTCC was collected by centrifugation at 14,000 rpm for 10 min. The resulting precipitate was washed three times with deionized H$_2$O and allowed to dry at room temperature and then freeze dried.

The formed nanocomposite was then characterized by transmission electron microscopy (TEM) and Dynamic light scattering analysis (DLS). The morphological structures of the nanocomposite obtained by electron microscopy indicated the great dispersion of the nanocomposite compound, which presented a compact surface with a highly porous structure. The particle size was in the range of 40-50 nm as indicated by DLS analysis.

Chitosan and silica are classified as Generally Recognized as Safe products (GRAS), designation of the United States Food and Drug Administration (FDA). Chitosan derived from crustaceans has GRN records No. 170 and 443, while amorphous synthetic silica has GRN records No. 321 and 298 at the FDA Example 4

Nanocomposite Activity Against Different Plant Pathogenic Fungi In Vitro

Three different concentrations (5, 10, and 25) mg/L of the nanocomposite were used in culture medium to test the percentage of mycelial growth of ten fungal pathogens, namely *Fusarium oxysporum*, *Fusarium solani*, *Alternaria solani*, *Alternaria alternata*, *Macrophomina phaseolina*, *Rhizoctonia solani*, *Verticillium dahliae*, *Magnaporthiopsis maydis*, *Fusarium verticillioides* and *Botrytis cinerea* after 7 days of incubation at 26±2° C. Variable effects of the nanocomposite on growth were observed. The fungal mycelial growth diameter was significantly decreased as nanocomposite concentrations increased.

Particularly, the nanocomposite at 5 mg/l concentration reduced the mycelial fungal growth by 77, 76, 78, 80, 83, 83, 88, 82, 90, and 100%, respectively, when compared to the control. A complete inhibition (100%) of the mycelial fungal growth of all the seven tested fungi (as examples) was obtained at 10, and 25 mg/l concentration, when compared to the control.

Example 5

Control of Maize Late Wilt Disease Caused by *Magnaporthiopsis maydis* Using the Nanocomposite as Seed Coating Agent The antifungal activity of the nanocomposite was further investigated in experiments in vivo aimed to control late wilt disease caused by *Magnaporthiopsis maydis* affecting maize plants. Disease severity was monitored for 120 days post inoculation (dpi) in corn plants grown from seeds treated with 1 mg/L of the nanocomposite after soil infection with the causal agent of late wilt.

Importantly, a significantly high reduction in disease severity of late wilt was observed in corn plants when their seeds were coated with the nanocomposite immersed in the nanocomposite solution before transplanting to the infectious soil. Disease severity was reduced 100% in corn plants treated with 1 mg/L of the nanocomposite (as an average of 3 independent experiments in 3 seasons).

Example 6

Nanocomposite Fungicidal Activity Against *Fusarium* Wilt

The antifungal activity of the nanocomposite was further investigated in experiments in vivo aimed to control *Fusarium* wilt disease affecting tomato plants. Disease severity was monitored for 75 days post inoculation (dpi) in tomato plants treated with 5 mg/L the nanocomposite after their soil infection with the causal agent of *Fusarium* wilt.

Importantly, a really high reduction in disease severity of both wilt was observed in tomato plants that were immersed for 5 minutes in the nanocomposite solution before transplanting to the infectious soil. Disease severity was reduced by 0% in tomato plants treated with 5 mg/L of the nanocomposite (as an average of 4 independent experiments, two seasons).

It is to be understood that the nanocomposite is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A nanocomposite comprising a water-soluble nano-polymer and mesoporous silica nanoparticles encapsulated with an azole derivative, the azole derivative having the formula I:

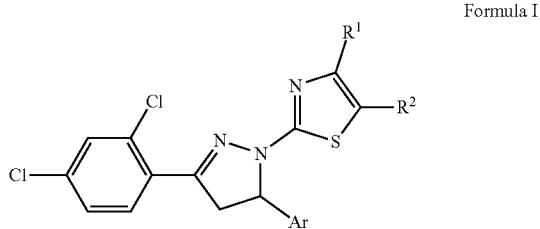

Formula I wherein,
R$_1$ is selected from methyl and substituted phenyl;
R$_2$ is selected from the group consisting of hydrogen, acetyl, ethyl carboxylate, N-phenyl carboxamide, phenyldiazenyl, p-tolyldiazenyl, and 4-(chlorophenyl) diazenyl; and
Ar is 4-methoxyphenyl or 3,4-dimethoxyphenyl.

2. The nanocomposite of claim 1, wherein the water-soluble nano-polymer is deposited on the pores of the mesoporous silica nanoparticles.

3. The nanocomposite of claim 1, wherein the nanocomposite has a particle size ranging from about 40 nm to about 50 nm.

4. The nanocomposite of claim 1, wherein the azole derivative has the formula Ia:

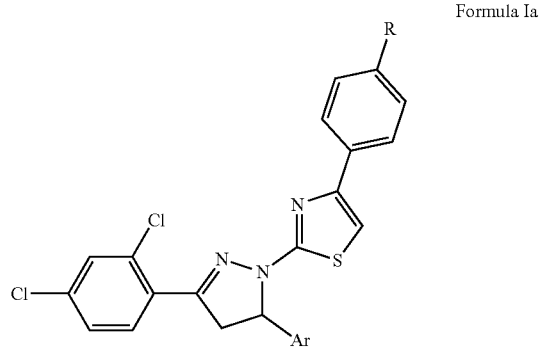

Formula Ia wherein,
R is H or Cl; and
Ar is 4-methoxyphenyl or 3,4-dimethoxyphenyl.

5. The nanocomposite of claim 1, wherein the water-soluble nano-polymer is chitosan.

6. The nanocomposite of claim 1, wherein the water-soluble nano-polymer is a quaternized chitosan.

7. The nanocomposite of claim 6, wherein the quaternized chitosan is N-(2-Hydroxyl) propyl-3-tri-methyl-ammonium CS chloride.

8. The nanocomposite of claim 1, wherein the mesoporous silica nanoparticles are NH$_2$-surface modified and functionalized with β-glucan.

9. The nanocomposite of claim 8, wherein the mesoporous silica nanoparticles are surface modified with a layer double hydroxide nanosheet (LDH).

10. The nanocomposite of claim 1, wherein the azole derivative is selected from the group consisting of 2-(3-(2,4-dichlorophenyl)-5-(3,4-dimethoxyphenyl)-4,5-dihydro-1H-pyrazol-1-yl)-4-phenylthiazole; 4-(4-chlorophenyl)-2-(3-(2,4-dichlorophenyl)-5-(3,4-dimethoxyphenyl)-4,5-dihydro-1H-pyrazol-1-yl)thiazole; 2-(3-(2,4-dichlorophenyl)-5-(4-methoxyphenyl)-4,5-dihydro-1H-pyrazol-1-yl)-4-phenylthiazole; and 4-(4-chlorophenyl)-2-(3-(2,4-dichlorophenyl)-5-(4-methoxyphenyl)-4,5-dihydro-1H-pyrazol-1-yl)thiazole.

11. A fungicidal composition, comprising the nanocomposite of claim 1 and a carrier.

12. The fungicidal composition of claim 11, wherein the carrier comprises at least one of a coloring agent and an anti-foaming agent.

13. A method of inhibiting fungal growth in a plant, comprising:
administering an effective amount of a fungicidal composition including a nanocomposite and a carrier to a plant in need thereof, the nanocomposite comprising chitosan nanoparticles and mesoporous silica nanoparticles encapsulated with an azole derivative, the azole derivative having the formula I:

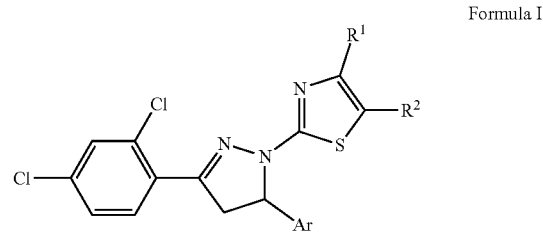

Formula I wherein,
R$_1$ is selected from methyl and substituted phenyl;
R$_2$ is selected from the group consisting of hydrogen, acetyl, ethyl carboxylate, N-phenyl carboxamide, phenyldiazenyl, p-tolyldiazenyl, and 4-(chlorophenyl) diazenyl; and
Ar is 4-methoxyphenyl or 3,4-dimethoxyphenyl.

14. The method of claim 13, wherein the administering of the fungicidal composition to the plant is selected from the group consisting of contacting the fungicidal composition with the plant, contacting the fungicidal composition with a seed of the plant, and contacting the fungicidal composition with soil surrounding the plant.

15. The method of claim 13, wherein the fungal growth is caused by a fungal pathogen selected from the group consisting of *Fusarium oxysporum, Fusarium solani, Alternaria solani, Alternaria alternata, Macrophomina phaseolina, Rhizoctonia solani, Verticillium dahliae, Magnaporthiopsis maydis, Fusarium verticillioides, Botrytis cinerea*, and any combination thereof.

16. The method of claim 15, wherein the fungicidal composition inhibits the growth of *F. oxysporum*.

17. The method of claim 15, wherein the fungicidal composition inhibits the growth of *Magnaporthiopsis maydis*.

18. An azole derivative having the formula I:

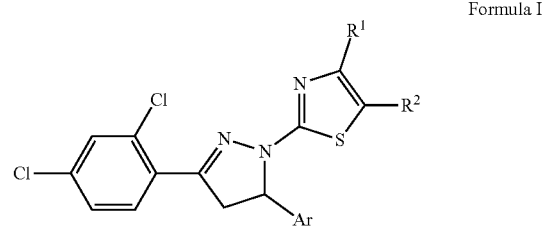

Formula I wherein,
R$_1$ is selected from methyl and substituted phenyl;
R$_2$ is selected from the group consisting of hydrogen, acetyl, ethyl carboxylate, N-phenyl carboxamide, phenyldiazenyl, p-tolyldiazenyl, and 4-(chlorophenyl) diazenyl; and
Ar is 4-methoxyphenyl or 3,4-dimethoxyphenyl.

19. The azole derivative of claim 18, wherein the azole derivative has the formula Ia:

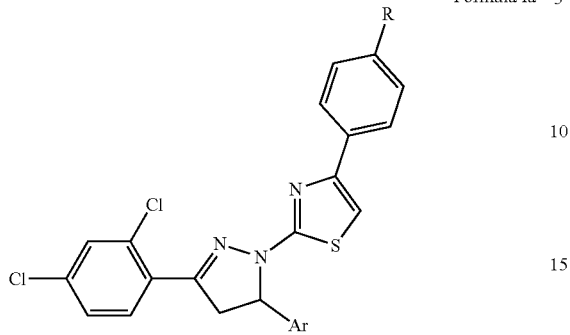

Formula Ia wherein,
R is H or Cl; and
Ar is 4-methoxyphenyl or 3,4-dimethoxyphenyl.

20. The azole derivative of claim 18, wherein the azole derivative is selected from the group consisting of 2-(3-(2,4-dichlorophenyl)-5-(3,4-dimethoxyphenyl)-4,5-dihydro-1H-pyrazol-1-yl)-4-phenylthiazole; 4-(4-chlorophenyl)-2-(3-(2,4-dichlorophenyl)-5-(3,4-dimethoxyphenyl)-4,5-dihydro-1H-pyrazol-1-yl)thiazole; 2-(3-(2,4-dichlorophenyl)-5-(4-methoxyphenyl)-4,5-dihydro-1H-pyrazol-1-yl)-4-phenylthiazole; and 4-(4-chlorophenyl)-2-(3-(2,4-dichlorophenyl)-5-(4-methoxyphenyl)-4,5-dihydro-1H-pyrazol-1-yl)thiazole.

\* \* \* \* \*

UNITED STATES PATENT AND TRADEMARK OFFICE
CERTIFICATE OF CORRECTION

| | | |
|---|---|---|
| PATENT NO. | : 11,805,773 B1 | Page 1 of 1 |
| APPLICATION NO. | : 18/211252 | |
| DATED | : November 7, 2023 | |
| INVENTOR(S) | : Mohamed Ahmed Mosa et al. | |

It is certified that error appears in the above-identified patent and that said Letters Patent is hereby corrected as shown below:

On the Title Page

Item (72), remove Inventor 1 residence "Al-Ahsa, SA" and replace with "Sohag, EG".

Signed and Sealed this
Nineteenth Day of December, 2023

*Katherine Kelly Vidal*

Katherine Kelly Vidal
*Director of the United States Patent and Trademark Office*